(12) United States Patent
Worobey et al.

(10) Patent No.: US 11,667,960 B2
(45) Date of Patent: Jun. 6, 2023

(54) METHODS AND SYSTEMS FOR RNA OR DNA DETECTION AND SEQUENCING

(71) Applicant: ARIZONA BOARD OF REGENTS ON BEHALF OF THE UNIVERSITY OF ARIZONA, Tucson, AZ (US)

(72) Inventors: Michael Worobey, Tucson, AZ (US); Thomas Watts, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 266 days.

(21) Appl. No.: 16/089,658

(22) PCT Filed: Apr. 20, 2017

(86) PCT No.: PCT/US2017/028591
§ 371 (c)(1),
(2) Date: Sep. 28, 2018

(87) PCT Pub. No.: WO2017/184845
PCT Pub. Date: Oct. 26, 2017

(65) Prior Publication Data
US 2019/0100793 A1    Apr. 4, 2019

Related U.S. Application Data

(60) Provisional application No. 62/325,320, filed on Apr. 20, 2016.

(51) Int. Cl.
*C12Q 1/6844* (2018.01)
*C12Q 1/70* (2006.01)

(52) U.S. Cl.
CPC ............ *C12Q 1/6844* (2013.01); *C12Q 1/70* (2013.01); *C12Q 1/703* (2013.01)

(58) Field of Classification Search
CPC ............................... C12Q 1/6844; C12Q 1/70
See application file for complete search history.

(56) References Cited

U.S. PATENT DOCUMENTS

| | | | | |
|---|---|---|---|---|
| 8,207,141 B2* | 6/2012 | Amici | .................... | A61P 35/04 514/44 R |
| 2005/0233314 A1* | 10/2005 | Juang | .................. | C12Q 1/6851 435/5 |
| 2006/0281108 A1* | 12/2006 | Monforte | .......... | C12Q 2525/204 435/6.16 |
| 2011/0311971 A1 | 12/2011 | Hartshorn et al. | | |
| 2012/0141989 A1 | 6/2012 | Chen et al. | | |
| 2014/0051585 A1* | 2/2014 | Prosen | ................. | B01J 19/0046 506/17 |
| 2014/0234830 A1* | 8/2014 | Exner | .................... | C12Q 1/701 435/5 |
| 2016/0289757 A1* | 10/2016 | Fleming | .............. | C12Q 1/6806 |

OTHER PUBLICATIONS

Quantabio, AccuStart Taq DNA Polymerase HiFi IFU, 2018. (Year: 2018).*
Fisher Scientific, Invitrogen Platinum Taq DNA Polymerase High Fidelity, 2020 (Year: 2020).*
Roche, LightCycler FastStart DNA Master SYBR Green I, 2018. (Year: 2018).*
Dolganov, A Novel Method of Gene Transcript Profiling in Airway Biopsy Homogenates Reveals Increased Expression of Na+-K+-Cl-Cotransporter (NKCC1) in Asthmatic Subjects, Genome Res., 11:1473-1483, 2001. (Year: 2001).*
Applied Biosystems, TaqMan® Universal PCR Master Mix, 2002. (Year: 2002).*
Tang et al. Quantitation of Taura syndrome virus by real-time RT-PCR with a TaqMan assay. J Virol Methods. 2004. vol. 115(1). p. 109-14.
Worobey et al. 1970s and 'Patient 0' HIV-1 genomes illuminate early HIV/AIDS history in North America. Nature. Nov. 3, 2016; 539(7627): 98-101.

* cited by examiner

*Primary Examiner* — Angela M. Bertagna
*Assistant Examiner* — Carolyn L Greene
(74) *Attorney, Agent, or Firm* — Nguyen Tarbet LLC

(57) ABSTRACT

Disclosed are methods and systems for detecting RNA and sequencing RNA in a wide range of samples such as samples with low concentrations of nucleic acid, samples with degraded nucleic acid, samples that would not otherwise be amenable to conventional sequencing or RNA detection methods, poor quality samples, high quality samples in which rare mutations are sought, formalin-fixed paraffin-embedded samples, blood samples, etc. The methods of the present invention may use paired, large panels of primers to amplify many short fragments that overlap between but not within each panel. Each panel's amplicon set may fill the gaps between those of the opposing panel, thereby providing complete gene or genomic coverage. A preliminary, multiplex amplification step amplifies target nucleic acid for all downstream reactions such as Sanger sequencing, cloning, and Next Generation Sequencing (NGS).

10 Claims, 2 Drawing Sheets

*Prior Art*

METHODS AND SYSTEMS FOR RNA OR DNA DETECTION AND SEQUENCING

GOVERNMENT SUPPORT

This invention was made with government support under Grant No. R01 AI084691 awarded by NIH. The government has certain rights in the invention.

FIELD OF THE INVENTION

The present invention relates to detection and sequencing of RNA or DNA, more particularly to detection and sequencing of RNA or DNA in samples with low concentrations of nucleic acid or poor quality samples. The present invention also features methods of detection and sequencing of viral RNA of viruses such as but not limited to human immunodeficiency virus (HIV), hepatitis C virus, hepatitis B virus, influenza virus, etc.

BACKGROUND OF THE INVENTION

In repositories around the world there are countless medical, veterinary, and museum specimens that would be valuable for the elucidation of the history and evolution of pathogens if (a) the pathogen can be detected and (b) genomic material of the pathogen can be amplified in sufficient length to be of phylogenetic use. For example, there are thousands of serum/plasma samples in storage worldwide from putative AIDS cases that go back to the 1970s and 1980s and that could elucidate both the epidemiological and evolutionary history of HIV. There are also thousands of samples that pre-date the recognition of AIDS, such as from hepatitis B studies that can yield valuable data regarding HIV, hepatitis C and other pathogens.

However, samples such as those describe above may have a low titer, e.g., the samples are degraded and/or may not be of the pathogen's target tissue. Some samples may have a low functional titer, e.g., there may be nucleic acids in the sample that represent the complete pathogen genome, but because of degradation there may be no nucleic acids long enough to complete a given PCR reaction, thus giving the sample an effective titer of zero (PCR-negative). Or, a given aliquot of sample nucleic acids used for testing may not contain the target sequence even though the sequence is present in the nucleic acid pool. In some cases, samples may have "cryptic" sequences (e.g., sequences that differ at some sites compared to known strains). For example, particularly with RNA viruses, there may be an issue related to sequence evolution. If one wants to investigate a sample that is 50 years old, and only modern sequences are available for primer design, then any given primer pair designed is only a rough guess as to the actual target sequence. Without wishing to limit the present invention to any theory or mechanism, it is believed that it in cases such as these, a single RT-PCR assay is liable to a miss, and designing around 'conserved regions' may also be inadequate. Another issue for samples is a limited quantity of the sample. In some cases, antiquated samples cannot be replicated and are often quite small.

Current or traditional strategies for detecting RNA and/or for phylogenetically viable amplification are discussed herein. Qpcr or single step RT and PCR assays are commercially available for many pathogens. They are designed to amplify a relatively short stretch of conserved sequence and so work well with some, but not all, samples of low functional titer and cryptic sequence. Because of their design, they do not yield useful phylogenetic data. Conventional RT-PCR (e.g., long form PCR) can be used for generating phylogenetically useful data. Attempts are often made to amplify PCR fragments of greater than 1000 bp. This method faces problems with poor sample quality since in such samples no such long template molecules may survive intact. Next Generation Sequencing (NGS) can develop long sequences, (often) whole genomes, from highly fractured specimens, and because amplification is not sequence based, has no issues with cryptic sequence. However, there is a minimum RNA titer that can be successfully amplified by NGS library technology (e.g., Ovation RNA Seq FFPE requires 100 to 200 ng RNA, see User Guide of Ovation RNA-Seq FFPE, pg. 8, "Total FFPE-derived RNA input must be in the range of 100 to 200 ng . . . input under 100 ng may result in insufficient yield for analysis."). There can also be problems with NGS if there is a low pathogen titer amongst a high titer of background (e.g. host) RNA.

Inventors surprisingly discovered methods and systems for detecting RNA and sequencing RNA in a wide range of samples, e.g., samples with low concentrations of nucleic acid, samples with degraded nucleic acid, samples that would not otherwise be amenable to conventional sequencing or RNA detection methods, poor quality samples, high quality samples in which rare mutations are sought (e.g. drug resistant clones), formalin-fixed paraffin-embedded (FFPE) samples, blood samples (e.g., serum or plasma samples), etc. For example, despite samples having no quantifiable RNA (thus being unusable according to NGS methods), Inventors were able to detect RNA and sequence RNA in said samples using methods of the present invention.

Briefly, methods of the present invention may use paired, large panels of primers to amplify many short fragments that overlap between (but not within) each panel. In some embodiments, each panel's amplicon set fills the gaps between those of the opposing panel, thereby providing complete gene or genomic coverage. A preliminary, multiplex amplification step, moreover, amplifies target RNA for all downstream reactions (including but not limited to Sanger sequencing, cloning, and NGS).

Inventors have tried conventional methods for recovering RNA in archival serum, plasma, or FFPE samples. For example, 53 serum samples from putative HIV infected individuals (1978, 1979) were tested with conventional PCR, which failed. RNA from samples was unquantifiable, thus it was not possible to use NGS. Using methods of the present invention, near full-length sequences were generated from 9 samples. The results of this study were published in the leading science journal Nature in 2016 to wide acclaim (Nature 539(7627)—October 2016). Additionally, forty-eight plasma or serum samples taken from patients displaying AIDS symptoms in Kinshasa in 1983 were serologically HIV-1-positive, but no HIV-1 RNA was recoverable using conventional PCR approaches at NIH, and the samples were deemed to be of no value. An initial screening run using methods of the present invention (based on non-overlapping 200 bp PCR fragments) designed to produce approximately 1300 bp of data generated greater than 75% of sequence target on the first run through in 46 samples (96%). Subsequently, a randomly selected 10 of these samples were subjected to a full panel of primer pools designed to cover the entire HIV coding region. Average yield after a first pass was 79% of total target sequence (high of 91%, low of 69%). It should be noted that these samples represent a wide variety of HIV subtypes including heretofore unknown subtypes indicating that this method is quite universal for HIV. These results indicate that it may be possible not only to recover HIV-1 RNA but also to generate near full-length sequences in the vast majority of such samples, even though they may appear to contain no recoverable RNA by previous methods. It should also be noted here that while this process is being done manually, currently available robotics, DNA quantification technology and automatic sequencing makes this technology highly scalable and automatable. FFPE samples from DRC, circa 1958-1966 were screened using an 8 primer assay (70-110 bp target length). HIV was detected in two samples (DRC60, DRC66). NGS sequencing of DRC66 has generated poor results to date. Approximately 450 bp of non-overlapping sequence was generated from DRC60 after extensive efforts using standard methods. Re-screening of the sample pool using methods of the present invention revealed an additional positive result, one of which was PCR-negative using previously applied conventional methods. Moreover, methods of the present invention with 192 primer pairs generated a near full-length sequence from DRC66 (>7000 bp).

The methods of the present invention may be used for a variety of applications. Applications may include but are not limited to: detecting RNA or DNA, detecting viral RNA (e.g., HIV RNA, etc.), detecting the presence (or absence) of a particular RNA, sequencing RNA, sequencing of RNA in a historical or poor quality sample, sequencing a plurality of variants of a particular RNA, e.g., viral RNA variants within a single sample, including rare, drug-resistant variants, etc. In some embodiments, the methods and systems of the present invention may be used for determining a range of hosts and vectors that may be susceptible to a virus infection; early and ongoing detection of viruses in emerging geographic ranges via rapid RT-PCR and sequencing of human and mosquito samples; bulk screening of travellers; and screening novel sources, for purposes of virus surveillance and tracking, e.g., municipal waste water; screening protocols allowing for screening of pools samples containing large numbers of individual organisms/mosquitos. Other applications may include but are not limited to: testing or screening whole blood samples (e.g., donated blood), e.g., providing higher sensitivity as compared to traditional methods, being capable of detecting presence of viruses earlier than serological testing or currently available nucleic acid testing; RNA detection, sequencing, or screening in cases where resources may be limited, since methods such as NGS may be too expensive; clinical diagnostics (e.g., HCV detection); vaccine research (e.g., for testing old, rare samples); kits for sequencing whole genomes; liquid biopsies (e.g., cancer biopsies); FFPE sample testing, etc.

The present invention is not limited to detection and/or sequencing of RNA. For example, the present invention also features methods for detecting and/or sequencing DNA. For example, the pre-amplification step may be used for detecting DNA viruses or other DNA targets.

As used herein, the term "conventional" may refer to Next Generation sequencing protocols that typically involve an RT-PCR amplification step of a sizeable viral genomic fragment, prior to Next Gen sequencing.

SUMMARY OF THE INVENTION

The present invention features methods for detecting a target (e.g., RNA, DNA) in a sample, or methods for sequencing a target (e.g., RNA, DNA) in a sample. In some embodiments, the method comprises subjecting the sample to reverse transcription (RT) using reverse transcriptase and one primer from each of one or more pairs of primers. The method may further comprise subjecting the sample from the previous step to polymerase chain reaction (PCR) amplification using Taq polymerase and the other primer of each of the one or more pairs of primers. The method may further comprise subjecting a portion of the sample from the previous step to PCR amplification using Taq polymerase and both of the primers from each of the one or more pairs of primers. The method may further comprise making detectable the amplified product of the PCR amplification (e.g., second PCR amplification with both of the primers from each of the pairs of primers. Detectable amplified product may be indicative of the presence of the target (e.g., RNA, DNA) in the sample.

The method may comprise subjecting the sample to reverse transcription using reverse transcriptase and a first primer from each of two or more pairs of primers comprising the first primer and a second primer, wherein, the first primers are non-overlapping with respect to each other, and the second primers are non-overlapping with respect to each other. The method may further comprise the sample from the previous step to polymerase chain reaction (PCR) amplification using Taq polymerase and the second primers of each of the pairs of primers. The method may further comprise subjecting a portion of the sample from the previous step to PCR amplification using Taq polymerase and both of the primers from each of the pairs of primers. The method may further comprise sequencing amplified products from the previous step.

The sample may be a sample of low quality. For example, the sample may not have quantifiable nucleic acid (e.g., RNA). In some embodiments, the sample comprises a low concentration of nucleic acid. In some embodiments, the sample comprises degraded nucleic acid. In some embodiments, the sample has low viral density. In some embodiments, the sample comprises a formalin-fixed paraffin-embedded (FFPE) sample. In some embodiments, the sample comprises serum or plasma.

In some embodiments, the primers have the same annealing temperature or are within 5 degrees of an average annealing temperature. The pairs of primers may each be adapted to amplify a fragment of the target from 60 nt to 300 nt (e.g., 60 to 70 nt, 70 to 80 nt, 80 to 100 nt, 100 to 150 nt, 150 to 200 nt, 200 to 300 nt, etc.) in length. In some embodiments, the fragment of the target from 60 nt to 300 nt in length includes the primer. The pairs of primers may each be adapted to amplify a fragment of the target from 60 nt to 600 nt (e.g., 60 to 70 nt, 70 to 80 nt, 80 to 100 nt, 100 to 150 nt, 150 to 200 nt, 200 to 300 nt, 300 to 400 nt, 400 to 500 nt, 500 to 600 nt, etc.) in length. In some embodiments, the fragment of the target from 60 nt to 600 nt in length includes the primer.

In some embodiments, the primers used in the reverse transcription (RT) step are non-overlapping. In some embodiments, the Taq polymerase is proofreading Taq polymerase.

In some embodiments, the target is a Retrovirus, e.g., human immunodeficiency virus (e.g. HIV-1, HIV-2). In some embodiments, the target is a Hepadnavirus (e.g. hepatitis B virus (HBV)). In some embodiments, the target is a Hepacivirus (e.g. hepatitis C virus (HCV)). In some embodiments, the target is a Flavivirus (e.g. yellow fever virus, west nile virus, dengue fever virus, Zika virus (ZIKV), etc.) In some embodiments, the target a Filovirus, e.g., an Ebolavirus (e.g., EBOV), Marbug virus (MARV). In some embodiments, the target is an Orthomyxovirus, e.g., an influenza virus (e.g., influenza virus A, influenza virus B, influenza virus C). In some embodiments, the target is a Paramyxovirus (e.g., Mumps virus (MuV), measles virus (MeV)). In some embodiments, the target is a Pneumovirus (e.g., a respiratory syncytial virus (RSV)). In some embodiments, the target is a Bunyavirus. In some embodiments, the target is a Togavirus (e.g., rubella virus). The present invention is not limited to the aforementioned targets or viruses since the methods of the present invention may be applied to any appropriate RNA detection application.

In some embodiments, the method further comprises isolating RNA from the sample prior to performing the RT step. In some embodiments, the method further comprises subjecting the sample to DNAse prior to the RT step.

The present invention also features kits for detecting or sequencing a target (e.g., RNA, DNA) in a sample. In some embodiments, the kit comprises two or more pairs of primers as described herein. For example, the pairs of primers comprise a first primer and a second primer. The pairs of primers may each be adapted to amplify a fragment of the target (e.g., RNA, DNA) from 60 nt to 600 nt (e.g., 60 to 70 nt, 70 to 80 nt, 80 to 100 nt, 100 to 150 nt, 150 to 200 nt, 200 to 300 nt, 300 to 400 nt, 400 to 500 nt, 500 to 600 nt, etc.). The first primers may be non-overlapping with respect to each other, and the second primers may be non-overlapping with respect to each other. The kit may further comprise reverse transcriptase. The kit may further comprise Taq polymerase. The kit may comprise 2 or more, 3 or more, 4 or more, 5 or more, 6 or more, 7 or more, 8 or more, 9 or more, 10 or more, 20 or more, 30 or more, 40 or more, 50 or more, 100 or more, etc., pairs of primers.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DETAILED DESCRIPTION OF THE INVENTION

Figure 1:
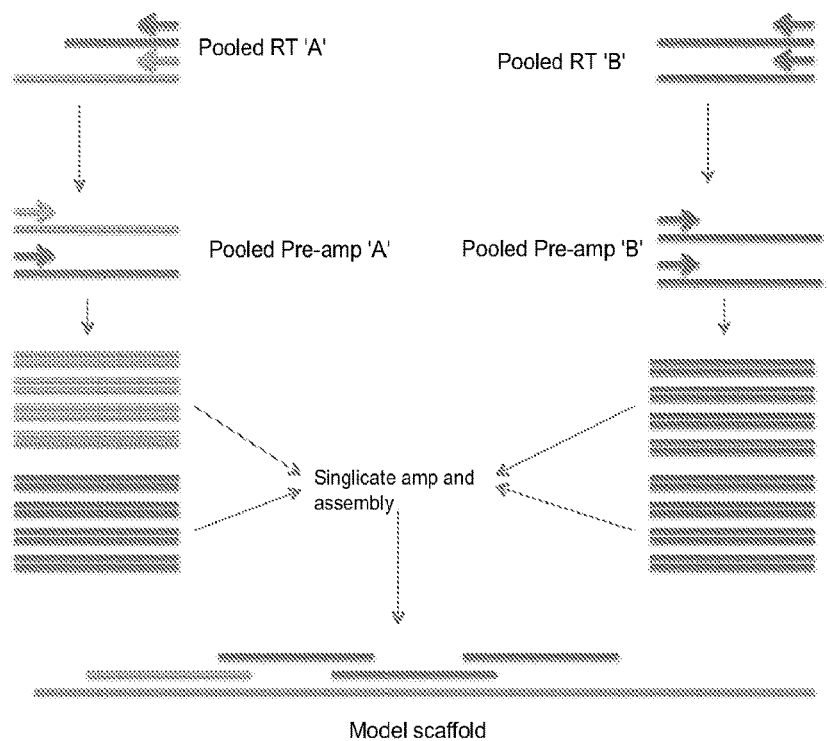
FIG. 1 shows a schematic view of an example of nucleic acid amplification methods of the present invention (and alignment of the amplicons).
Figure 3:
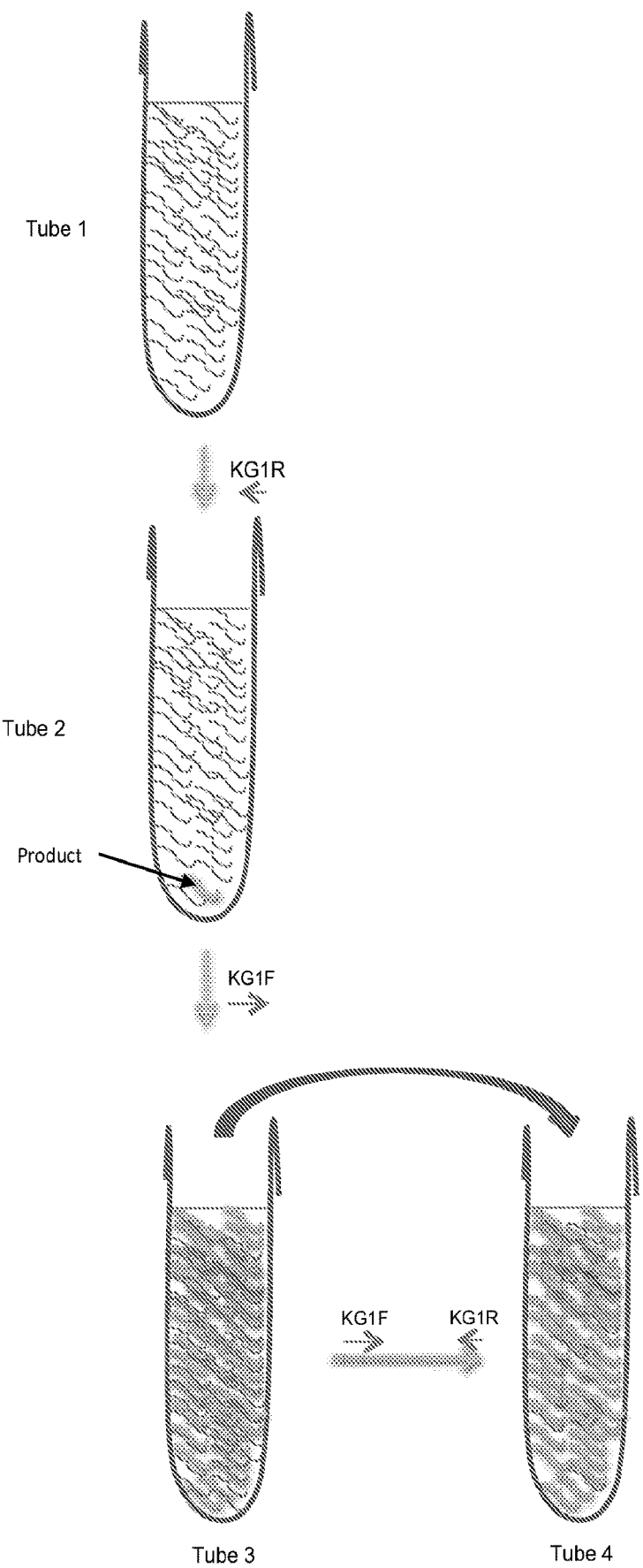
FIG. 3 shows a schematic view of the methods of the present invention used for the detection and amplification of a target molecule in an old, degraded, low titer sample. Note that this schematic view is a simplified schematic. For example, instead of 1 pair of non-overlapping primers, there may be 10 or more (and 10 or more final amplifications). (Note the present invention is not limited to 1 pair, or 10 or more pairs of primers.) Tube 1: As a example, in this tube there are $10^{13}$ RNA molecules, but only one molecule that is both capable of being primed by primer KG1R and long enough to form an 80 bp product when amplified with primers KG1F/KG1R. In Tube 1, RT is performed with $10^7$ molecules of KG1R. There is one usable product. Tube 2 shows RT is then performed with $10^7$ molecules of KG1R. There is one usable product. Tube 3 shows amplification with $10^7$ molecules of KG1F and proofreading Taq. After 20 amplification cycles, there are $10^5$ usable products. An aliquot (e.g., 10% of the product) is transferred to Tube 4 and amplified in a PCR reaction with primers KG1F and KG1R. There is essentially a 100% chance that this will be a positive sample. As an example, with a 10 primer pool and 10 final reactions, there is potential to get 10 amplicons for sequencing.

Referring now to FIG. 1 and FIG. 3, the present invention features methods and systems for detecting RNA or DNA in a wide range of samples, e.g., samples with low concentrations of nucleic acid, samples with degraded nucleic acid, samples that would not otherwise be amendable to conventional sequencing or RNA detection methods, poor quality samples, high quality samples, formalin-fixed paraffin-embedded (FFPE) samples, blood samples (e.g., serum or plasma samples), breast milk samples, archival serum/plasma, etc. The present invention also features methods and systems for sequencing of RNA in said samples. The present invention also features methods of detecting or sequencing viral nucleic acid.

Methods of the present invention may be used for detection and phylogenetically relevant amplification of pathogens (e.g., RNA viruses) for which sequence data can only be guessed at, and are difficult, fractured and low titer samples. For example, when attempting to detect and amplify sequence from, for example, fifty-year-old HIV samples, modern sequences can be of only limited use in designing primers.

Methods of the present invention feature using panels of primer pairs. For example, in some embodiments, the methods of the present invention use panels (e.g., 8-10) of primer pairs (e.g., degenerate primers, non-degenerate primers) for detection. In some embodiments, the methods of the present invention use panels (e.g., 8-10) of non-degenerate primer (or a mix of degenerate and non-degenerate primers) for detection. In some embodiments, the methods of the present invention use 50-200 primer pairs (e.g., degenerate, non-degenerate, a combination thereof) for near full-length sequencing. Methods of the present invention also feature a pre-amplification step of RT products so as to increase titer prior to final PCR. This helps allow for adequate sequence yield from some samples that have immeasurably low yields of RNA and/or are highly fractured. Because methods of the present invention may be designed to amplify 1000-1500 bp of sequence from a given aliquot of native RNA, sample size may be much less a factor than if each PCR fragment was generated from a separate RT reaction. In the case of the 1978, 1979 serum samples mentioned above, near full-length sequence could be generated using only 30 ul of 50 ul serum eluate generated from 50-100 ul of serum.

The present invention also features methods of detecting or sequencing genetic variations of RNA (e.g., variations of the RNA within the same sample), e.g., detecting within-host viral genetic variation with phenotypic consequences (e.g., on drug resistance, pathogenesis, cell/tissue tropism, transmissibility to secondary hosts, etc.). Without wishing to limit the present invention to any theory or mechanism, it is believed that the methods of the present invention may help to detect genetic variations that are not necessarily apparent when large amplicons are generated. For example, variations in primer regions in some clones may prevent them from being amplified. Also, the effective template number of large amplicons may be much smaller than small amplicons (e.g., there may only be one or a few template molecules 1000 nt in length in a degraded sample whereas there may be more template molecules shorter in length). In the present invention, if several 100 nt regions within that same region are separately assayed, there may be orders of magnitude more template molecules and thus a chance to observe within-patient diversity that may otherwise be invisible when aiming for a larger fragment.

As previously discussed, the methods of the present invention feature targeting several small fragments of the target RNA. For example, in some embodiments, the fragment that is targeted is about 70 nt in length. In some embodiments, the fragment is about 80 nt in length. In some embodiments, the fragment is about 90 nt in length. In some embodiments, the fragment is about 100 nt in length. In some embodiments, the fragment is about 110 nt in length. In some embodiments, the fragment is from 65 to 90 nt in length. In some embodiments, the fragment is from 70 to 100 nt in length. In some embodiments, the fragment is from 70 to 110 nt in length. In some embodiments, the fragment is from 80 to 100 nt in length. In some embodiments, the fragment is from 100 to 200 nt in length. In some embodiments, the fragment is from 70 to 200 nt in length. The present invention is not limited to the aforementioned examples. For example, in some embodiments, the fragment is more than 200 nt in length, e.g., from 200 to 250 nt, from 200 to 300 nt, from 300 to 400 nt, from 400 to 500 nt, etc. Fragment size may depend on the quality of the sample.

In some embodiments, at least 2 primer pairs are used. In some embodiments, at least 3 primer pairs are used. In some embodiments, at least 4 primer pairs are used. In some embodiments, at least 5 primer pairs are used. In some embodiments, at least 6 primer pairs are used. In some embodiments, at least 7 primer pairs are used. In some embodiments, at least 8 primer pairs are used. In some embodiments, at least 9 primer pairs are used. In some embodiments, at least 10 primer pairs are used. In some embodiments, at least 20 primer pairs are used. In some embodiments, at least 30 primer pairs are used. In some embodiments, at least 40 primer pairs are used. In some embodiments, at least 50 primer pairs are used. In some embodiments, at least 75 primer pairs are used. In some embodiments, at least 100 primer pairs are used. In some embodiments, at least 150 primer pairs are used. In some embodiments, at least 200 primer pairs are used. The present invention is not limited to the aforementioned examples, and more than 200 primer pairs may be used.

In some embodiments, 2 primer pairs are used. In some embodiments, 3 primer pairs are used. In some embodiments, 4 primer pairs are used. In some embodiments, 5 primer pairs are used. In some embodiments, 6 primer pairs are used. In some embodiments, 7 primer pairs are used. In some embodiments, 8 primer pairs are used. In some embodiments, 9 primer pairs are used. In some embodiments, 10 primer pairs are used. In some embodiments, 11 primer pairs are used. In some embodiments, 12 primer pairs are used. In some embodiments, 13 primer pairs are used. In some embodiments, 14 primer pairs are used. In some embodiments, 15 primer pairs are used. In some embodiments, 16 primer pairs are used. In some embodiments, 16 primer pairs are used. In some embodiments, 18 primer pairs are used. In some embodiments, 19 primer pairs are used. In some embodiments, 20 primer pairs are used. In some embodiments, 21 primer pairs are used. In some embodiments, 22 primer pairs are used. In some embodiments, 23 primer pairs are used. In some embodiments, 24 primer pairs are used. In some embodiments, 25 primer pairs are used. In some embodiments, 26 primer pairs are used. In some embodiments, 27 primer pairs are used. In some embodiments, 28 primer pairs are used. In some embodiments, 29 primer pairs are used. In some embodiments, 30 primer pairs are used. In some embodiments, 40 primer pairs are used. In some embodiments, 50 primer pairs are used. In some embodiments, 100 primer pairs are used. In some embodiments, 200 primer pairs are used. As previously discussed, the present invention is not limited to the aforementioned examples, and more than 200 primer pairs may be used.

The primer pairs may be divided into at least 2 pools. In some embodiments, 2 pools are used. In some embodiments, 3 pools are used. In some embodiments, 4 pools are used. In some embodiments, 5 pools are used. In some embodiments, 2 pools are used. In some embodiments, 6 pools are used. In some embodiments, 7 pools are used. In some embodiments, 8 pools are used. In some embodiments, 9 pools are used. In some embodiments, 10 pools are used. In some embodiments, more than 10 pools are used. In some embodiments, pools have about 10 primers each.

For example, in some embodiments, when attempting to detect the presence of a particular RNA, about 8 to 10 primer pairs may be used. In some embodiments, when attempting to sequence a particular RNA, about 50 primer pairs may be used. However, the present invention is not limited to the aforementioned examples.

As previously discussed, the present invention may help sequence RNAs in historical samples of unknown subtypes, as well as sequence variants of an RNA. Without wishing to limit the present invention to any theory or mechanism, it is believed that the use of multiple, small fragments may be advantageous for sequencing unknown subtypes or RNAs with polymorphisms.

Example 1—Plasma/Serum Samples

Example 1 describes an example of a protocol for plasma/serum samples. The present invention is not limited to the details of Example 1. This example describes a procedure for working up a sample using 40 overlapping primer pairs designed to generate products of approximately 200 bp. This will provide 6000+ bp of sequence. Actual amount of sequence is a function of how much overlap designed into the primers. For FFPE samples or severely degraded liquid samples, 70-100 bp primer pairs may be designed. High quality proof-reading Taq is used. This protocol uses Promega Goscript and RNAsin plus for RT. Taq is Accustart.

Make up 4 forward primer pools (A, B, C, D) and 4 matching reverse primer pools (A, B, C, D). The following schematic may be used (for both forward group and reverse group):

|  | Pool A | Pool B | Pool C | Pool D |
|---|---|---|---|---|
| Primer # | 1 | 2 | 3 | 4 |
| Primer # | 5 | 6 | 7 | 8 |
| Primer # | 9 | 10 | 11 | 12 |
| Primer # | 13 | 14 | 15 | 16 |
| Primer # | 17 | 18 | 19 | 20 |
| Primer # | 21 | 22 | 23 | 24 |
| Primer # | 25 | 26 | 27 | 28 |

-continued

|         | Pool A | Pool B | Pool C | Pool D |
|---------|--------|--------|--------|--------|
| Primer #| 29     | 30     | 31     | 32     |
| Primer #| 33     | 34     | 35     | 36     |
| Primer #| 37     | 38     | 39     | 40     |

Reverse Transcription:

For each sample to be amplified, the following may be used: Primer/dNTP: Make up 4 reverse primer/dntp pools, one for each of A,B,C,D. (1) Primer—9 ul, (2) dNTP—3 ul. Add 4 ul of 'A' to wells 1 and 5 of an 8 place strip. Add 'B' to wells 2 and 6 and etc. Then add 6 ul sample to each of wells 1-4 and 6 ul control to wells 5-8. Mix well. Incubate at 70 C for 5'. Ice. RT mix: (1) 5× buffer—36 ul; (2) 25 mM Mg—36 ul; (3) RNasin—9 ul; (4) Goscript—9 ul. Add 10 ul per sample, mix well and incubate at 42 C for 2 hours, followed by 10' at 85 C.

Preliminary amplification: The following may be used: Add 4 ul 'A' forward primer pool to wells 1 and 5 of an 8 place strip, and 4 ul of 'B' to wells 2 and 6 and etc. Master mix: 10×—45 ul; 50 mM Mg—18 ul; dNTP—9 ul; Taq—4 ul; Water—252 ul. 36 ul mix into each well. Add 10 ul individual RT reaction the appropriate well. Mix well. Amplify for 30 cycles in a standard PCR program at the appropriate annealing temperature (e.g., primers may be designed around 52 degrees C.).

Final amplification: The following may be used: Make up 5×8 well strips with individual primer pairs in numerical order as in schema below (e.g., 2 ul primer total per well). One may want one set for the sample and one for the control.

|         | Well 1    | Well 2    | Well 3    | Well 4    | Well 5    | Well 6    | Well 7    | Well 8    |
|---------|-----------|-----------|-----------|-----------|-----------|-----------|-----------|-----------|
| Strip 1 | Primer 1  | Primer 2  | Primer 3  | Primer 4  | Primer 5  | Primer 6  | Primer 7  | Primer 8  |
| Strip 2 | Primer 9  | Primer 10 | Primer 11 | Primer 12 | Primer 13 | Primer 14 | Primer 15 | Primer 16 |
| Strip 3 | Primer 17 | Primer 18 | Primer 19 | Primer 20 | Primer 21 | Primer 22 | Primer 23 | Primer 24 |
| Strip 4 | Primer 25 | Primer 26 | Primer 27 | Primer 28 | Primer 29 | Primer 30 | Primer 31 | Primer 32 |
| Strip 5 | Primer 33 | Primer 34 | Primer 35 | Primer 36 | Primer 37 | Primer 38 | Primer 39 | Primer 40 |

Make up 8 Master mixes, four for samples (A,B,C,D) and four for controls (A,B,C,D). Master mix: 10×—27.5 ul; 50 mM Mg—11 ul; dNTP—5.5 ul; Taq—1 ul; Pre-amp product—22 ul; Water—187 ul. Add 23 ul of Sample 'A' master mix to primer wells 1 and 5 of each strip, Master mix Sample 'B' to wells 2 and 6 and etc. as per schema above. Mix well. Amplify for 40 cycles at appropriate annealing temperature.

In some embodiments, this protocol, e.g., when used in conjunction with appropriately designed primers, may generate 70-90% of the target sequence on the first go through. Note that some products may be double banded with a contaminating human band, so some gel clipping may be required unless going to NGS sequencing. Note that when the first go round is done, there is 10 ul leftover RT reaction for each pool of each sample. This can be used to pre-amp and amp on an alternative cycling program such as a Touchdown program to generate bands that cover some of the blank spots. In some embodiments, this step is done before going to sequencing. Once sequencing is done and the sequences are lined up with the primers, new primers may be designed to match missing sequence. Note also that this protocol may help ensure that no given amplification is exposed to confounding internal primers from the primer pairs immediately upstream or downstream of the amplification. This may help ensure that mis-incorporation of primers doesn't compromise the data.

Example 2—Recovery of HIV Sequences from Degraded Archival Samples

Methods of the present invention for recovering viral RNA were used test 1970s HIV serum samples (degraded archival samples). Example 2 describes the recovery of eight near-full-length genomes from US serum samples from 1978-79—eight of the nine oldest HIV-1 group M genomes to date. Example 2 also describes recovery of the HIV-1 genome from the individual known as 'Patient 0' (Auerbach et al, 1984, Am J Med 76: 487-492) (showing there is neither biological nor historical evidence he was the primary case in the US or for subtype B as a whole).

HIV-1 Serological Screening of Serum Samples from San Francisco from 1978.

2231 samples collected from the cohort of gay and bisexual men in San Francisco in 1978 (Jaffe et al., 1985, Ann Intern Med 103: 210-214) were tested, and 83 WB-positives were detected (3.7% prevalence). Samples were first screened by GS HIV-1/HIV-2 Plus O EIA (Bio-Rad Laboratories, Redmond Wash.) and reactive samples were further tested by WB Genetic Systems HIV-1 Western Blot (Bio-Rad Laboratories, Redmond Wash.).

HIV-1 Nucleic Acid Amplification.

A total of 33 samples of frozen serum previously identified as positive for antibody to HIV-1 (Stevens et al, 1986, JAMA 255: 2167-2172; Szmuness et al, 1981, Hepatology 1: 377; Koblin et al., 1992, J Epidemiology 136:646-656) were assayed from New York City; a total of 20 frozen serum samples from San Francisco (Jaffe et al., 1985, Ann Intern Med 103: 210-214), identified as part of the present study as positive for antibody to HIV-1, were assayed. The New York City samples were from 1978 and 1979 though no complete genomic sequences from 1978 were developed. The San Francisco samples were all from 1978. Additionally, a sample of PMBC and a sample of serum were both assayed; these had been collected from a single individual in 1983 (Patient 0), and the samples were stored at CDC Atlanta. Other than Patient 0, now deceased, the data recorded were unlinked to individual identifiers and the work was approved by the Human Subjects Protection Program at the University of Arizona.

Four panels of degenerate primers were designed using a suite of North American subtype B sequences. Primers were designed to be able to amplify both conserved regions and predictably variable sites. Primers within each panel were designed to generate sequence from the 5' end of gag to the 3' end of nef and were designed to amplify overlapping fragments. Two panels "HIVL" (N=25) and "HIVLb" (N=22) were designed to amplify fragments of ~500-650 bases in length. Two other panels "HIVm" (N=50) and "HIVr" (N=46) were designed to amplify fragments of ~200-320 bases in length. Nucleic acids from 100 ul aliquots of serum (or PMBCs in the case of Patient 0) were isolated using the QIAamp Viral RNA Mini Kit (Qiagen, Gaithersburg, Md.) with 5 mcg added carrier RNA. Serum samples were then treated with DNase I (Invitrogen, Life Technologies, Carlsbad, Calif.) prior to reverse transcription. PMBC nucleic acids were left untreated. Proviral DNA from Patient 0's PMBCs was amplified with all four primer panels and from multiple separate isolations. Amplification was achieved using Invitrogen Platinum Taq DNA polymerase High Fidelity (Life Technologies, Carlsbad, Calif.) and run for 55 cycles at an annealing temperature of 52° C. Additionally, attempts were made to amplify longer fragments using PCR SuperMix High Fidelity (Life Technologies, Carlsbad, Calif.) and forward and reverse primers matched from the HIVLb primer panel for long fragment length followed by nesting with primers for slightly shorter fragment length. A single fragment of slightly more than 7000 bases was generated after multiple attempts with multiple primer combinations and cloned using the Invitrogen TOPO XL PCR Cloning Kit (Life Technologies, Carlsbad, Calif.). Fragments of individual clones were then amplified using HIVLb forward and reverse primers matched to give approximately 1000-base overlapping fragments and then sequenced.

Methods of the present invention using the serum samples proceeded as follows: Aliquots of isolated RNA were reverse transcribed using the GoScript Reverse Transcription System (Promega, Madison, Wis.) using a program of 4 cycles of 50° C. for 30' followed by 55° C. for 30' and an 85° C. final incubation. Primers used were pools of reverse primers from widely spaced amplicons, abrogating the possibility of incorporation of an internal primer into any given amplicon. RT products were then briefly amplified in multiplex reactions (denaturation for 3' at 94° C. followed by 30 cycles of 94° C. for 30", 52° C. for 30", 68° C. for 30", and a final extension of 68° C. for 5') with matching forward primer pools and then amplified via single primer pairs (denaturation for 3' at 94° C. followed by 40 cycles of 94° C. for 30", 52° C. for 30", 68° C. for 30", and a final extension of 68° C. for 5'). Two separate isolates were amplified from each sample in this manner with a minimum of one amplification with each primer panel per isolate. Sequencing was performed at the University of Arizona Genetics Core using an ABI 3730XL. The Patient 0 sample contained considerable heterogeneity (mixed bases) both in proviral assembly and in viral RNA amplifications. Heterogeneity in the NY and SF samples (all sequences derived from viral RNA) was low. In all cases consensus sequences were used in the phylogenetic analyses.

Example 3—Viral Enrichment and Multiplex RT-PCR Viral Genetic Screening Assays

Example 3 describes the development of viral enrichment and multiplex RT-PCR viral genetic screening assays that are more sensitive than existing RT-PCR protocols for detection of viral RNA. The methods of the present invention could allow recovery of viral genomic information from challenging source material (e.g., specimens with low concentration of template viral RNA, samples containing no viable (culturable) virus, etc.). The methods of the present invention may be useful in conventional samples as well, e.g., for conventional samples in resource-limited settings where culturing of virus may be precluded but RT-PCR may be possible. Without wishing to limit the present invention to any theory or mechanism, it is believed that the methods of the present invention may allow for detection of viral RNA with very high sensitivity (e.g., up to 100% specificity after sequencing). Thus, this may allow for the use of the methods of the present invention in resource-limited settings (e.g. without the need for culturing viral isolates), for detecting viral RNA in low-concentration, damaged or otherwise challenging samples (e.g., pooled mosquito specimens, archival human specimens, or perhaps even municipal influent (e.g., sewage) samples), etc.

In some embodiments, the methods of the present invention feature RNA (or DNA capturing, e.g., for concentration of viral nucleic acids from large pooled samples. This may increase the chances of finding the target sequence and may be effective at sequestering target nucleic acids away from potential inhibitors.

Referring to FIG. 3, the methods further comprise using non-degenerate and/or degenerate primers directed to a wide spectrum of viral strains, which are designed to amplify 70-100 nt fragments in overlapping fashion (e.g., for FFPE samples) or 200-300 nt fragments (e.g., for serum/plasma). Primers are then pooled in non-overlapping fashion for reverse transcription, and then a 'preliminary-amplification' (pre-amplification) step is employed to amplify with corresponding primer mates. The pre-amplified mix is then broken up for amplification with single primer pairs. The pre-amplification step greatly increases the effective titer of the target molecules, thus increasing both sensitivity and coverage.

Figure 2:
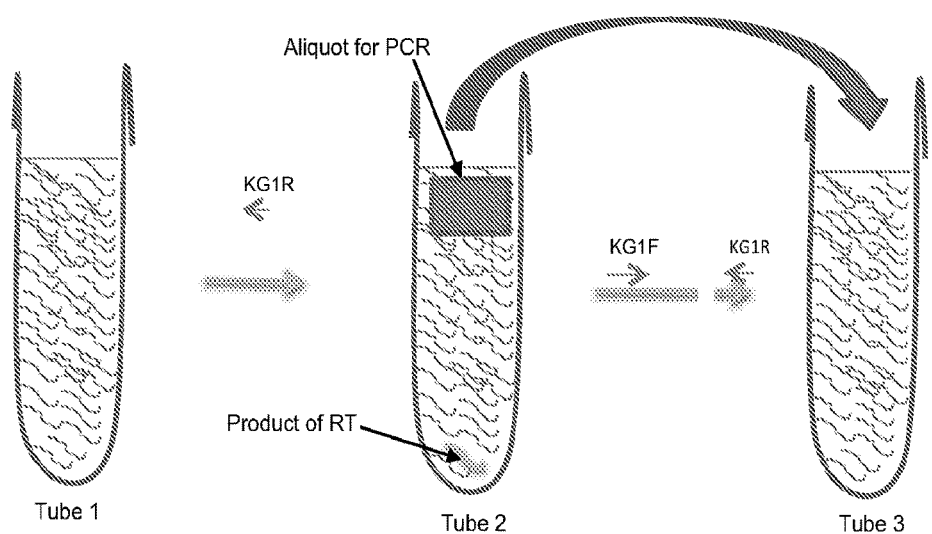
FIG. 2 (PRIOR ART) shows a schematic view of conventional amplification methods used for the detection and amplification of a target RNA molecule in an old, degraded, low titer sample. Tube 1 (left tube): As an example, in this tube there are $10^{13}$ RNA molecules, but only one molecule that is both capable of being primed by primer KG1R and long enough to form an 80 bp product when amplified with primers KG1F/KG1R. RT is performed with $10^7$ molecules of KG1R. There is one usable product (Tube 2, middle tube). PCR amplification is performed on a subsample (aliquot) of Tube B (e.g., 10% of Tube B) using primers KG1F and KG1R. There is a large chance (e.g., about a 90% chance) that this (Tube 3, right tube) will be a negative sample.

This technique allows for HIV detection that is not otherwise detectable using previous techniques (see FIG. 2) and for development of long sequences by alignment of overlapping short sequences in samples that would otherwise be recalcitrant to viral genome sequencing. This technique provides a greater degree of assurance that a virus can be identified in samples with very low copy number and/or damaged RNA. Without wishing to limit the present invention to any theory or mechanism, it is believed that sequencing short reads in samples that have damaged RNA increases the likelihood of detecting polymorphisms.

Bell et al., 1971. *Arch. Gesamte Virusforsch.* 35:183-193; Calisher et al., 1989. *J. Gen. Virol.* 70:37-43; Crill et al., 2004. *Cell* 78:13975-13986; Dick et al., 1952. *Trans. R. Soc. Trop. Med. Hyg.* 46:509-20; Duffy et al., 2009, *N Engl J Med.* 360: 2536-2543; Faye et al., 2014. *PLOS, Neglected Tropical Diseases.* DOI: 10.1371/journal.pntd.0002636; Fischer and Hayes, 2009. *N. Engl. J. Med.* 360:2536-2543; Hayes, 2009. *Emerg. Infect. Dis.* 15:1347-1350; Kuno et al., 1998. *J. Virol.* 72:73-83. Gilbert et al., 2007. *PLoS ONE* 2: e537. Lanciotti et al., 2008; *Emerg. Infect. Dis.* 14:1232-1239; Messina et al., 2014. *Trends Microbiol.* 22:138-146. Elsevier Ltd; Mlakar et al., 2016. *N. Engl. J. Med.* 160210140106006; Rolland et al., 2012, Nature 490: 417-420; Smith et al., 2014, J Virol. Am Soc Microbiol 88: 9976-9990; Tofanelli et al., 1999. *Ancient Biomolecules*, V2, pp. 307-320; Wagner et al., 2014, Science 345(6196): 570-573; Worobey et al., 2008. *Nature* 455, 661-6641; Worobey et al., 2014. *Proc Nati Acad Sci USA.* 104: 18566-18570; Worobey et al., 2016. *Nature* 539, 98-101; Xu et al., 2015. *Science* 348(6239).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of detecting a target RNA in a sample, said method comprising:
    (a) subjecting the sample to reverse transcription using reverse transcriptase and one primer from each of two or more pairs of primers, the pairs of primers are each adapted to amplify a fragment of the target RNA from 60 nt to 300 nt in length, wherein the target RNA is non-detectable using conventional RNA detection methods;
    (b) adding the other primer from each of the two or more pairs of primers and subjecting the sample of (a) to multiplex polymerase chain reaction (PCR) amplification using Taq polymerase and both primers of each of the two or more pairs of primers;
    (c) aliquoting a portion of the sample from (b), and subjecting the portion of the sample from (b) to PCR amplification using Taq polymerase and at least one pair of primers of the two or more pairs of primers; and
    (d) detecting amplified product of (c), wherein detectable amplified product of (c) is indicative of the presence of the non-detectable target RNA in the sample.

2. The method of claim 1, wherein each of the two or more pairs of primers have the same annealing temperature or are within 5 degrees of an average annealing temperature.

3. The method of claim 1, wherein the fragment of the target RNA from 60 nt to 300 nt in length includes the primer.

4. The method of claim 1, wherein one or more of the primers used in (a) are non-overlapping.

5. The method of claim 1, wherein the sample comprises degraded nucleic acid.

6. The method of claim 1, further comprising subjecting the sample to DNAse prior to step (a).

7. A method of detecting and sequencing viral nucleic acid in a sample, said method comprising:
    (a) subjecting the sample to reverse transcription using reverse transcriptase and a first primer from each of two or more pairs of primers, the pairs of primers are each adapted to amplify a fragment of the viral nucleic acid from 60 nt to 600 nt in length, wherein the first primers are pooled into at least two primer pools;
    (b) adding the second primer from each of the two or more pairs of primers to the primer pools and subjecting the sample of (a) to multiplex polymerase chain reaction (PCR) amplification using Taq polymerase and both primers of each of the two or more pairs of primers;
    (c) aliquoting a portion of the sample from (b), and subjecting the portion of the sample from (b) to PCR amplification using Taq polymerase and at least one pair of primers of the two or more pairs of primers; and
    (d) detecting and sequencing amplified products of (c).

8. The method of claim 7, wherein the method detects genetic variations in the viral nucleic acid.

9. The method of claim 7, wherein the first primer comprises a reverse primer, and the second primer comprises a corresponding forward primer.

10. The method of claim 7, wherein the first primers from each of two or more pairs of primers used in (a) are non-overlapping.

* * * * *